United States Patent [19]

Paskar

[11] Patent Number: 5,304,131
[45] Date of Patent: Apr. 19, 1994

[54] CATHETER

[76] Inventor: Larry D. Paskar, 14337 Stablestone Ct., Chesterfield, Mo. 63017

[21] Appl. No.: 834,007

[22] Filed: Feb. 11, 1992

Related U.S. Application Data

[63] Continuation-in-part of Ser. No. 730,120, Jul. 15, 1991.

[51] Int. Cl.$^5$ .............................................. A61M 37/00
[52] U.S. Cl. ...................... 604/95; 604/281; 128/658
[58] Field of Search ............... 604/95, 281, 280, 164, 604/165, 264; 128/4, 656–658, 772

[56] References Cited

U.S. PATENT DOCUMENTS

| | | | |
|---|---|---|---|
| 4,236,509 | 12/1980 | Takahashi et al. | 128/4 |
| 4,353,358 | 10/1982 | Emerson | 128/4 |
| 4,586,923 | 5/1986 | Gould et al. | 604/95 |
| 4,850,351 | 7/1989 | Herman et al. | 128/4 |
| 4,898,577 | 2/1990 | Badger et al. | 604/95 |
| 4,911,148 | 3/1990 | Sosnowski | 128/4 |
| 4,935,017 | 6/1990 | Sylvanowicz | 604/281 |
| 5,109,830 | 5/1992 | Cho | 604/95 |

FOREIGN PATENT DOCUMENTS

| | | |
|---|---|---|
| 2923633 | 12/1980 | Fed. Rep. of Germany . |
| 2130885 | 6/1984 | United Kingdom ............ 128/4 |

Primary Examiner—John D. Yasko
Assistant Examiner—Mark Bockelman
Attorney, Agent, or Firm—Polster, Lieder, Woodruff & Lucchesi

[57] ABSTRACT

A medical tube has at least one wire running from the proximal end to the vicinity of the distal end thereof, which wire is connected to the tube adjacent the distal end so as to allow the distal tip to be deflected upon movement of the wire. The tube has gaps therein on one side of its longitudinal axis so as to form a predetermined region of weakness, whereby upon tension being applied to the wire the distal end of the tube bends in the direction of the predetermined region of weakness. The medical tube may be a sheath in which is disposed a preformed inner catheter having a complex curve formed into the distal end thereof. The sheath is sufficiently rigid and the inner catheter is sufficiently pliable so that withdrawal of the inner catheter into the sheath substantially straightens out the portion of the complex curve of the distal tip disposed within the sheath. By suitable manipulation of the wire and of the inner catheter with respect to the sheath the shape of the exposed portion of the distal end of the inner catheter may be reformed and transformed to any of a variety of shapes as desired by the user.

10 Claims, 5 Drawing Sheets

CATHETER

CROSS REFERENCE TO RELATED APPLICATION

This application is a continuation in part of U.S. application Ser. No. 07/730,120, filed Jul. 15, 1991 now pending.

BACKGROUND OF THE INVENTION

This invention relates generally to medical devices, and more particularly to a catheter which can be formed, inside the human body, into a vast number of different shapes.

Selective catheterization of cerebral and visceral branch arteries is often difficult and at times impossible in some patients—particularly older patients with very tortuous and ectatic vasculature. Successful catheterization sometimes requires multiple catheter exchanges for various shaped catheters. It is not uncommon to easily catheterize three of four vessels for a four vessel head study, only to find that the fourth vessel (generally the left or right carotid) requires an entirely different catheter shape and tip orientation. It would be desirable if one could easily and simply reshape the catheter and reorient the tip to direct it into the vessel orifice, instead of depending on several complex catheters that require reformation, fancy torque and advancing maneuvers, body english and, above all, luck.

Tip reorientation, the goal of most prior devices which have addressed the problem, is only half of what is needed to make a truly workable universal catheter. Numerous catheter curve configurations have been conceived not only to reorient the tip properly for selection of branch vessels, but also to provide anchorage of the catheter against the aortic wall. A wide looped long tipped sidewinder III configuration with an exaggerated retrocurve is one such example of a highly specialized complex catheter.

This anchorage or wedge effect against the aortic wall lessens the recoil caused by the "jet effect" during high pressure contrast injection which might otherwise cause the catheter to flip out of the selected branch vessel (particularly in short branch vessels or at levels of a dilated aorta).

These complex configurations, therefore, evolved not only to orient the tip properly, but also to wedge the catheter securely in the branch vessel. Other devices which simply modify the distal catheter curve may aid in tip orientation for vessel selection, but fail to provide the anchorage which is necessary to prevent catheter dislodgement.

In addition, prior designs could be improved in that the radii which the prior devices are able to make (to enter a vessel at a sharp angle, for example) have heretofore been severely limited.

Moreover, the size of prior designs has made them less desirable for many applications.

In certain applications (for example, complex interventional procedures such as angioplasties or intracerebral procedures), current catheters could be improved with respect to their ability to facilitate crossing of tight stenoses or with respect to their trackability out into peripheral branches.

In this respect, the current catheters could be improved in the areas of displacing forces from the application site at the point of catheter introduction (most often in the inguinal area) to points close to the actual catheter tip. This would increase the control that a user, such as an angiographer, has on the catheter, creating a more precise local longitudinal vector force for crossing tight stenoses, and also increase torque force for guiding the catheter tip toward the orifice of a selected vessel.

In would also be desirable to have a catheter construction which provided controllable variability in the distal catheter stiffness. Such a catheter could be stiffened for support close to a first order selected branch through which a more flexible catheter could be tracked peripherally. Conversely, such a catheter could be made less stiff over variable distances to allow better tracking of a more flexible distal end over a guidewire.

SUMMARY OF THE INVENTION

Among the various objects and features of the present invention may be noted the provision of a catheter which simplifies the catheterization procedure.

A second object is the provision of such a catheter which significantly reduces the number of catheterizations required for any particular medical procedure.

A third object is the provision of such a catheter which can be easily and simply reshaped into a variety of different shapes as desired by the user.

A fourth object is the provision of such a catheter which can mimic almost any catheter configuration, and can thereafter be reformed in the body to other desired shapes.

A fifth object is the provision of such a catheter which obviates the need for multiple catheter exchanges, thereby reducing the time involved in a medical procedure and also reducing the possibility of complications.

A sixth object is the provision of such a catheter which provides adequate anchorage of the catheter against the aortic wall to reduce the "jet effect."

A seventh object is the provision of such a catheter which capable of achieving an improved curve radius at its distal end.

An eighth object is the provision of such a catheter which is significantly reduced in size compared to the prior devices.

A ninth object is the provision of such a catheter which will displace longitudinal vector force from the site of application in the groin of the patient to a point near the tip of the catheter, thereby facilitating the crossing of tight stenoses during angioplasty procedures.

A tenth object is the provision of such a catheter which will displace torque force from the site of application in the groin of the patient to a point near the tip to facilitate more precise torque of the catheter tip, improving the ability to enter selected vessels.

An eleventh object is the provision of such a catheter which will provide variable stiffness at the distal end that will facilitate catheter advancement peripherally when it serves as a stiffened support near a first order take off vessel and will likewise facilitate tracking over a guidewire when made more flexible over a variable distance, distally.

Other objects will be in part apparent and in part pointed out hereinafter.

Briefly, a catheter of the present invention includes a catheter tube having a wall and an internal lumen extending substantially through the length of the catheter tube, the catheter tube having an outside diameter sufficiently small so that the catheter tube may be inserted into the human body and having a proximal end and a distal end. At least one wire runs from the proximal end of the catheter tube to the vicinity of the distal end of the catheter tube, which wire is connected to the catheter tube adjacent the distal end so as to allow the distal tip of the catheter tube to be deflected upon movement of the wire. The catheter tube has a substantially uniform transverse cross section throughout a substantial part of its length, and the catheter tube wall adjacent the distal end of the catheter tube has gaps therein on one side of the longitudinal axis of the catheter tube so as to form a predetermined region of weakness. Upon tension being applied to the wire, the distal end of the catheter tube bends in the direction of the predetermined region of weakness.

In a second aspect of the present invention, a transformable catheter includes a sheath having a diameter sufficiently small so that the sheath may be inserted into blood vessels of the human body, the sheath having a length which is a substantial fraction of the entire length of the transformable catheter. The sheath also has a bore therethrough running substantially from the proximal end of the sheath to the distal end of the sheath. A preformed inner catheter has a complex curve formed into the distal end thereof, and is sized to fit in the sheath bore. The inner catheter is axially movable with respect to the sheath in the bore, the sheath being sufficiently rigid and the inner catheter being sufficiently pliable so that withdrawal of the inner catheter into the sheath substantially straightens out the portion of the complex curve of the distal tip contained within the sheath. The distal tip resumes its complex curve shape upon movement thereof out of the sheath bore. The user axially moves the inner catheter with respect to the bore to expose only so much of the distal end of the inner catheter as to cause the exposed portion of the distal end of the inner catheter to take a desired shape. The inner catheter has a length substantially corresponding to the length of the transformable catheter. At least one wire runs from the proximal end of the sheath to the vicinity of the distal end of the sheath, the wire being connected to the sheath adjacent the distal end so as to allow the distal tip of the sheath to be deflected upon movement of the wire. By suitable manipulation of the wire and of the inner catheter with respect to the sheath, the shape of the exposed portion of the distal end of the inner catheter may be reformed and transformed to any of a variety of shapes as desired by the user. The sheath has at its distal end a predetermined region of weakness so that upon tension being applied to the wire, the distal end of the sheath bends in the direction of the predetermined region of weakness.

Although the invention is described in connection with blood vessels, it is not so limited. It may be used not only in arterial and venous branches, but also in the biliary tree, urinary tract, body cavities (such as the thorax and abdomen), hollow viscous organs (such as the stomach, intestines, and urinary bladder), cysts and abscesses—in short, in any place where selective direction and reformation of a catheter, tube or guidewire is required.

BRIEF DESCRIPTION OF THE DRAWINGS

Similar reference characters indicate similar parts throughout the several views of the drawings.

DESCRIPTION OF THE PREFERRED EMBODIMENT

Figure 1A:
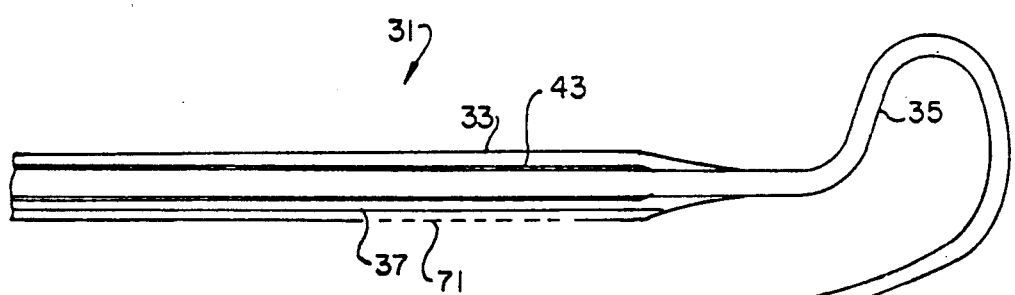
FIGS. 1A-1B, and 1D are side elevations illustrating the construction of the transformable catheter of the present invention.
Figure 1B:
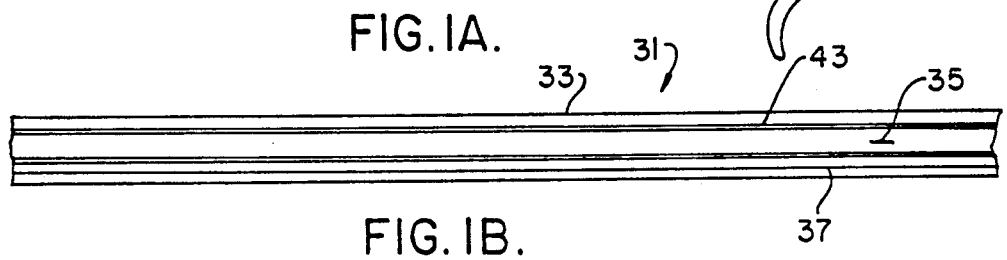
Figure 1C:
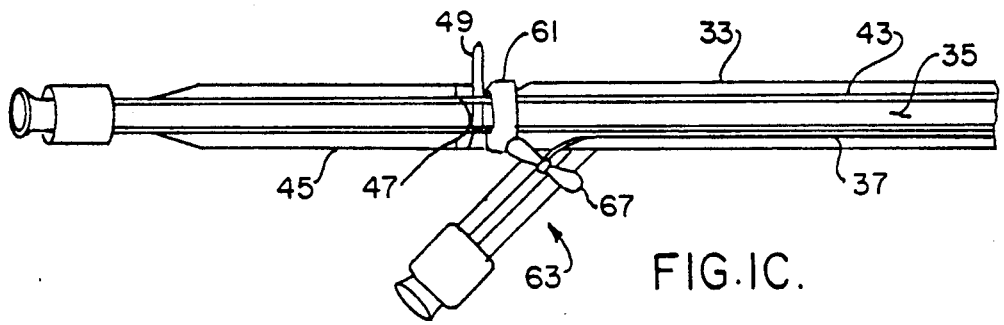
FIG. 1C is a top plan of the proximal portion of the transformable catheter of the present invention.

A catheter 31 (see FIGS. 1A-1C) of the present invention in its simplest form includes an enabling sheath 33, and an inner catheter 35 having a distal tip with a complex-curve shape. Catheter 31 is especially suited for selective arterial catheterization. In that application, the catheter is custom shaped or formed while in the patient to make it easy to direct the tip in any orientation required to enter a branching orifice or serpiginous vessel. Catheter 31 is not a steerable catheter, but rather one which may be custom curved and recurved by the user to select each branch vessel. The catheter may also be used in the biliary tree and urinary tract to negotiate branches, corners, and serpiginous pathways.

As will become apparent in view of the following disclosure, manipulation of catheter 31 results in mimicking virtually any simple or complex curved configuration of selective arterial catheter shape imaginable while the catheter is disposed in the patient. Likewise, modification of curve and tip orientations allow selection and direction of wire guides for other invasive procedures such as percutaneous cholangiography and percutaneous nephrostomy; that is, any procedure requiring direction or redirection of a catheter.

Inner catheter 35 is a complex memory curve catheter which runs in a coaxial manner through enabling sheath 33. With the complex tip completely extended beyond the sheath, the most complex tip configuration reforms. By pulling the inner catheter back through the enabling sheath to varying degrees (sheathing and unsheathing the inner catheter tip), various segments of the curve are straightened or "ironed out"—thereby changing the overall catheter tip configuration and tip orientation. The inner catheter is the active primary component but is a passive passenger with respect to the enabling sheath which acts upon the catheter to modify its shape. In addition, the fact that the transformation takes place in a vessel in the human body further modifies the shapes which can be achieved due to interaction of the transformable catheter with the walls of the vessel.

Sheath 33 has the capability of being formed by a pullwire 37 into a hook configuration, as described below. (Although described as a wire, item 37 could equivalently be made of high tensile strength suture or thread material.) This capability allows reformation of the complex memory curvature by directing the catheter tip downward while transformable catheter 31 is disposed in the aorta. Secondarily the sheath curve can, to some degree, act on the catheter to further modify the catheter shape.

In detail, transformable catheter 31 (see FIGS. 1A–1C) includes outer enabling sheath 33 which extends almost the entire length of the catheter. It is preferred that sheath 31 be long enough so that only the complex curve distal end portion of the inner catheter extend beyond it. Inner catheter 35 is disposed in the central bore of sheath 33 and has the most exaggerated sidewinder preformed tip configuration distally. (Of course, any other similar complex-shaped memory curve inner catheter could also be used in the present invention as inner catheter 35.)

The distal end of enabling sheath 33 can be formed into a curve with up to one hundred and eighty degrees of curvature when retracted by pull wire 37 by the suitable application of tension to the pull wire. This allows the hook configuration of the sheath 33 to reform the catheter 35 when the catheter is advanced through the sheath. The variable curved tip also allows variation in the degree of curvature, modifying the natural memory curve and thereby the overall shape of the catheter.

Figures 2A, 2B, 2C, 2D:
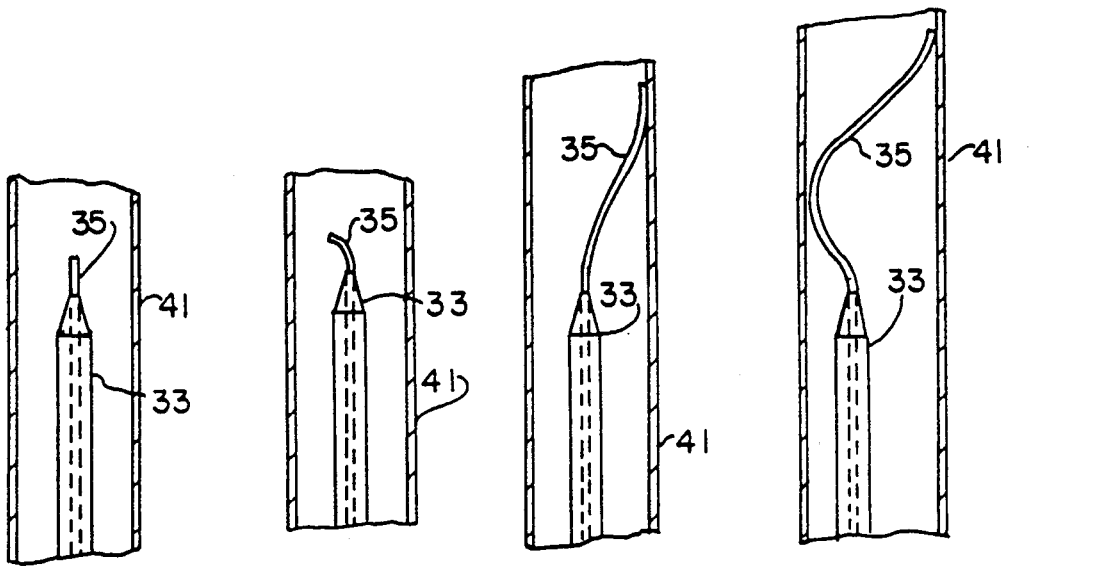
FIGS. 2A-2D are simplified elevations illustrating some of the myriad shapes which are attainable with the transformable catheter of the present invention.

Enabling sheath 33 modifies the extreme natural curvature of catheter 35 by acting as a housing that irons out various segments of the curvature when the catheter is retracted back into the sheath. Such an "ironing" effect is illustrated in FIG. 2A. In FIGS. 2 and 3, the various portions of transformable catheter 31 are shown in simplified form for clarity. For example, in FIG. 2A, the catheter 35 is shown extending distally from sheath 33 a small amount, while catheter and sheath are disposed in a vessel (such as an artery) 41.

In FIG. 2B, the same catheter 35 is shown extended distally out of sheath 33 a small additional amount such that the catheter regains some of its curvature. Similarly, in FIGS. 2C and 2D, catheter 35 is extended distally even further. Note that in FIG. 2D, the distal curved portion of catheter 35 is fully extended from sheath 33, but the original configuration of catheter 35 is not obtained because of the interaction of the catheter with vessel wall 41.

Figures 3A, 3B, 3C:
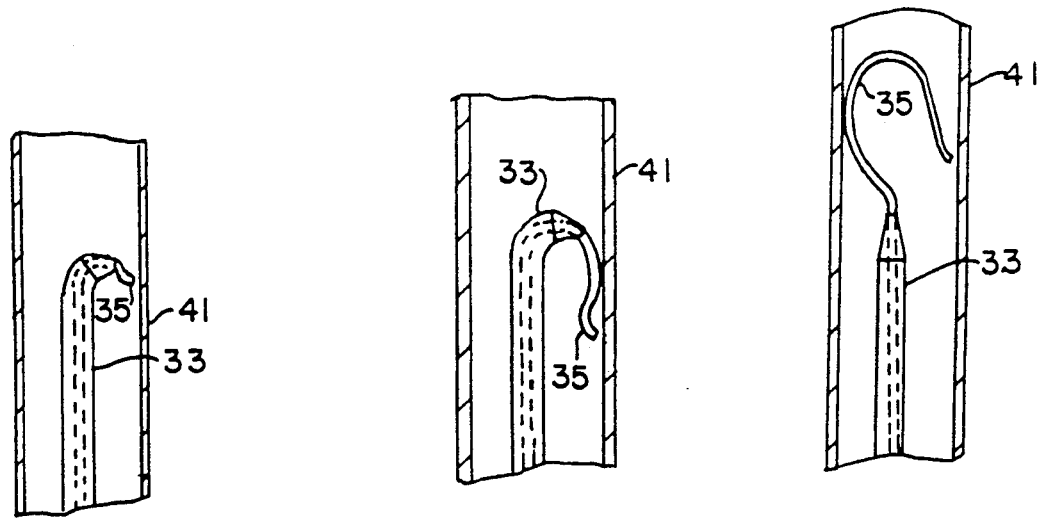
FIGS. 3A-3C are simplified elevations illustrating the reformation of a complex catheter shape inside the human body.

If the physician desires to instead shape or form catheter 35 back into its original, preformed shape of FIG. 1, the steps illustrated in FIGS. 3A–3C are followed. In this case, the sheath is first formed (by use of retraction wire 37) into the shape shown in FIG. 3A and FIG. 3B. As a result of this shape of the sheath, as catheter 35 is moved distally with respect to the sheath it assumes the form in the vessel as illustrated in FIGS. 3A and 3B. The sheath is restraightened by suitable manipulation (i.e., release) of retraction wire 37 as shown in FIG. 3C as desired. This procedure allows the original form of catheter 35 to be obtained in the vessel.

Note, from comparing FIG. 2D with FIG. 3C, the great differences in catheter shape achievable by simple manipulation of sheath 33 and of the catheter with respect to the sheath. In fact FIGS. 2A–2D and 3A–3C all illustrate some of the multitude of different catheter shapes which may be formed in the body, during a medical procedure, using the present invention. It should be realized that these shapes are merely illustrative and that with suitable manipulation of the sheath and relative movement between the sheath and the catheter, a great number of additional catheter configurations may be achieved.

Note as well, that the particular configuration shown in FIG. 3B provides a tighter radius for the tip of catheter 31 than is achievable with prior devices due to the interaction of complex-formed tip of the inner catheter and the deflection of the sheath. This greater flexibility in the shapes achievable permits vessels to be entered with the present catheter which were not readily accessible with the prior devices.

Referring back to FIGS. 1A–1C, the inner catheter 35 travels through the enabling sheath in a coaxial manner, but is stiffened from its proximal end to a point just proximal to the distal exaggerated curvatures by an outer stiffening segment 43. This outer stiffening segment is fused to the inner catheter proximally and distally and provides sufficient strength to the inner catheter to permit it to be moved axially with respect to the sheath without collapsing or binding.

Transformable catheter 31 is introduced in the usual manner through the femoral artery and advanced into the abdominal aorta. The catheter is reformed and selectively shaped in the abdominal aorta. When initially introduced the inner catheter is in its straightened parked position within the enabling sheath with only a small distal tip segment protruding (see FIG. 2A). The pull wire 37 is retracted, forming a hooked curve (see FIG. 3A) which allows direction of the catheter tip downward and thereby easy reformation of the memory curve. Once reformed, the various shapes of the catheter can be selected by advancing or retracting the catheter into the enabling sheath, thereby allowing or disallowing the natural memory curves to form at various segments. Pull wire modification of the enabling sheath allows additional curved configurations.

Figure 1D:
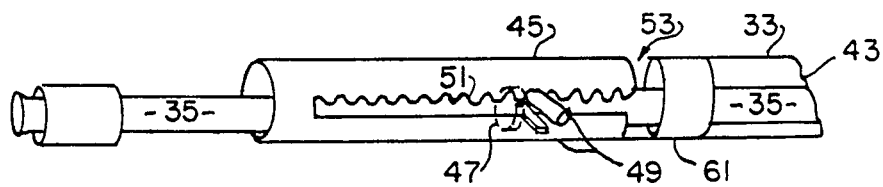
Figure 1E:
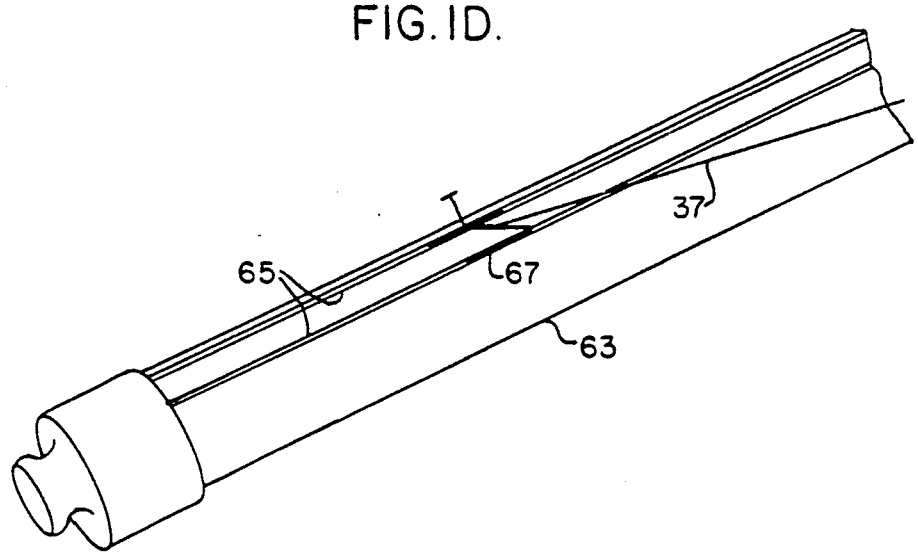
FIG. 1E is a view, similar to FIG. 1D but on an enlarged scale, illustrating the construction of a side port of the transformable catheter of the present invention.

Proximally, the stiffened inner catheter is pulled back through a plastic sleeve 45, slotted on either side. (See FIGS. 1C and 1D.) A fixation collar 47 attaches to the proximal portion of the catheter. A molded spring "V" prong 49, rounded on one side and flat on the other, arises from the side of the collar and extends through the sleeve. The prong is fixedly secured to catheter 35 and can be pulled through a right slot 51 of the sleeve (see FIG. 1D), thereby pulling the catheter as a whole through the enabling sheath and ironing out various degrees of memory curve in the distal tip of the catheter. The spring "V" prong 49 when squeezed together passes freely through the slot whose border is straight inferiorly but serrated superiorly as shown in FIG. 1D. When released the prong springs open and the rounded segment locks in a chosen serrated position. Distally, a crossing slot 53 allows the prong to be pulled across to the left slot (similar in size and shape to the right slot 51 shown), thereby twisting and torquing the entire catheter one hundred and eighty degrees so that when the prong 49 is pulled back in the left slot position the curved configuration is ironed out, resulting in additional variations in catheter shape. The locking pattern of the left slot is opposite to that of the right —flat upper border, serrated lower border, still allowing collar locking in various retracting positions.

The inner catheter proximally must exit through a valve (such as hemostasis valve 61 shown in FIG. 1C) as found in current arterial sheaths. A "Y" branch side port 63 allows constant pressure flushing of the sheath to prevent possible clot formation and allows water activation of the hydrophilic retraction wire.

On top of the side port 63, slide tracks 65 (see FIG. 1E) are molded. The tracks contain a plastic "S" spring slide 67 with locking teeth. The slide spring is attached to the pull wire 37 proximally. As the slide spring is disengaged by pushing downward and pulling back, the wire is retracted. When released the "S" slide locks into the selected position in the track. When straightening of the enabling sheath is desired, the slide 67 is disengaged and pushed to the forward position, thereby releasing traction on the wire and allowing the enabling sheath to reform spontaneously or with help by sliding the reinforced catheter towards the tip or by placing a straightening wire guide through the inner catheter lumen.

The ventral primary curvature segment of the enabling sheath is biased (as indicated at the reference numeral 71, FIG. 1A) to curve in a desired direction by making the sidewall along the inner portion of the desired curve more flexible due to the type or thickness of the material in this segment. Similarly, a flexibility bias can be established by designing exposed or covered gaps along one side of a segment of the sheath over which the bend is desired. When pulled distally, the more flexible or gapped side of the segment will give first, thereby, allowing curvature in a precisely selected segment and direction.

Although heretofore the invention has been described with respect to a transformable catheter with a controllable sheath and a complex curved inner catheter, the present invention is not so limited. The inventive aspects of the controllable sheath are applicable in general to medical tubing, including catheters. It should be understood, therefore, that a reference herein to "sheath" should be understood in the broader sense of medical tubing, which includes catheters.

Figure 4A:
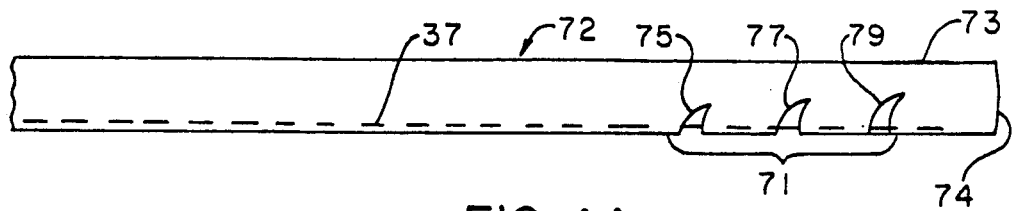
FIGS. 4A-4D are partial elevations illustrating operation of one embodiment of the present invention.

Turning to FIG. 4A, a sheath or catheter 72 of the present invention includes a medical tube 73 having an exterior wall and an internal lumen extending substantially through the length of the tube. The tube has an outside diameter sufficiently small so that it may be inserted into the human body. The distal end 74 of tube 73 is shown in FIG. 4A.

Wire 37 runs from the proximal end of the tube to the vicinity of the distal end of the tube, and, in the same manner as described above in connection with FIG. 1, is connected to the tube adjacent the distal end so as to allow the distal tip of the tube to be deflected upon movement of the wire. The tube has a substantially uniform transverse cross section throughout a substantial part of its length, except for the distal tip section. The tube wall adjacent the distal end has gaps 75, 77, and 79 therein on one side of the longitudinal axis of the catheter tube so as to form a predetermined region of weakness 71. As a result, upon tension being applied to the wire the distal end of the catheter tube bends in the direction of the predetermined region of weakness.

Figure 4B:
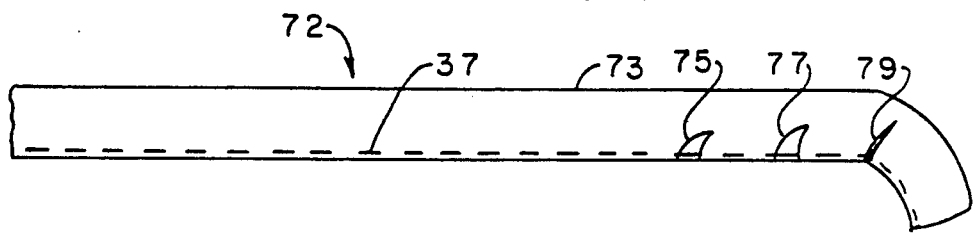
Figure 4C:
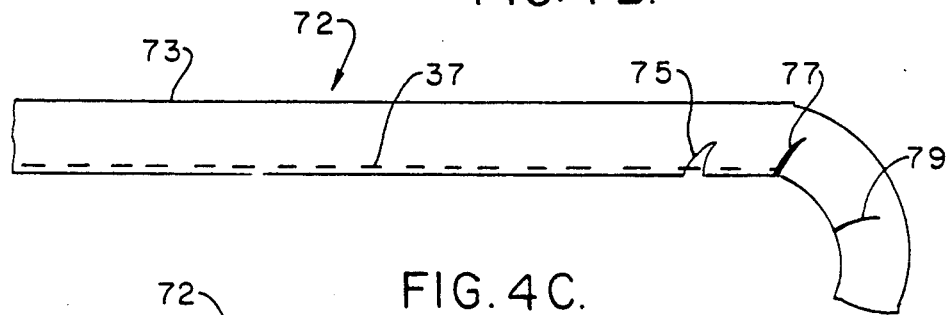
Figure 4D:
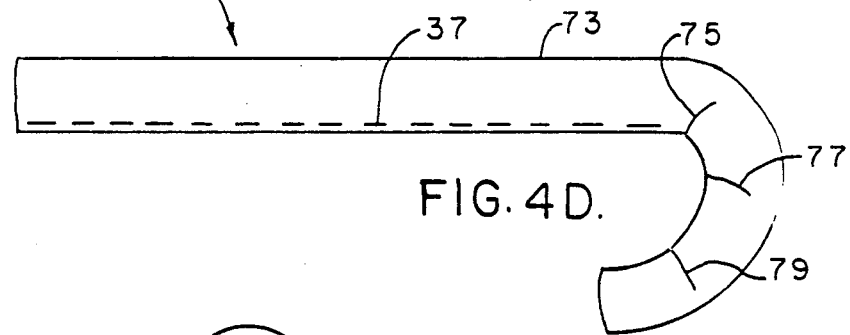

Although gaps 75, 77, and 79 can all be the same size, it is preferred that they differ in size as shown in FIG. 4A. The three gaps of FIG. 4A differ in depth, as can readily be seen. It has been found that with this construction the catheter or sheath preferentially bends first at the gap with the greatest depth (gap 79), and next at the gap with the second greatest depth (gap 77), and finally at the gap with the least depth (gap 75), as shown in FIGS. 4B-4D, as increasing tension is applied to wire 37.

Figure 5:
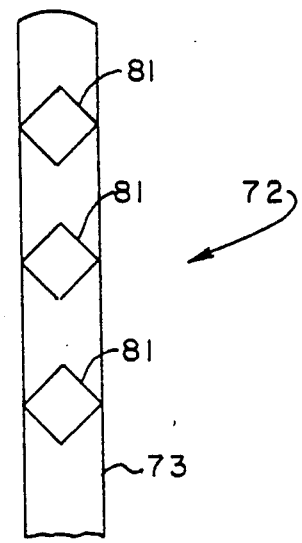
FIG. 5 is a partial elevation illustrating a gap shape different from that shown in FIGS. 4A-4D.
Figure 6:
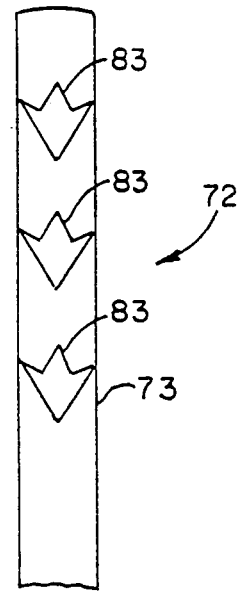
FIG. 6 is a view similar to FIG. 5 illustrating another gap shape.

Although gaps 75, 77 and 79 of FIG. 4 are generally crescent moon shaped, the present invention is not limited to any particular gap shape. For example, gaps 81 having a generally diamond shape (FIG. 5), or gaps 83 having a compound arrowhead shape (FIG. 6), or any of a number of other gap shapes may also be used. Gaps shaped so that portions of the catheter tube wall on opposite sides of each gap may overlap when the catheter is formed by the wire to have its greatest curvature may be used, as may gaps shaped so that there is no overlap (although overlapping can provide a tighter curve on the distal end of the sheath/catheter). Similarly, gaps shaped so that the distal wall portion overlaps the proximal wall portion of the gap when the catheter is formed by the wire to have its greatest curvature may be used, as may gaps shaped so that the proximal wall portion overlaps the distal wall portion of the gap.

Figure 7:
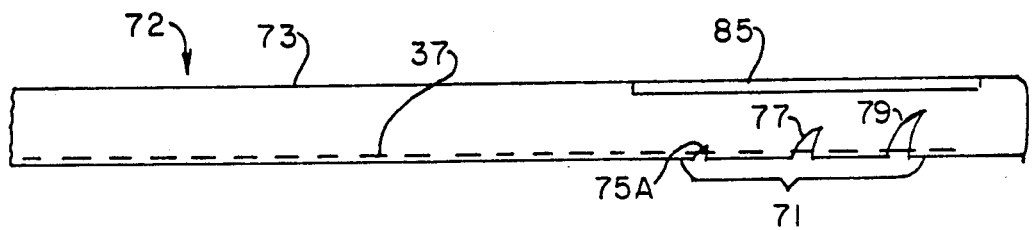
FIG. 7 is a view similar to FIG. 4A illustrating an alternative construction.

Nor is there any rigid requirement concerning depth of gap. Although the gaps of FIG. 4 extend through the walls of the sheath/catheter to the lumen, that is not a requirement. In FIG. 7, for example, a gap 75A is provided which terminates short of the sheath/catheter lumen. It still helps provide the desired predetermined region of weakness 71. Also shown in FIG. 7 is a reinforcing section 85 which may, for example, be co-extruded with the sheath/catheter. This reinforcing section may be used in combination with the gaps, or by itself, to cause the distal end of the sheath/catheter to bend in the direction of region 71 when tension is applied to wire 37.

No matter what the shape of the gap, it is preferred that the inner surface of the gap adjacent the lumen of the catheter be smooth.

Figure 8:
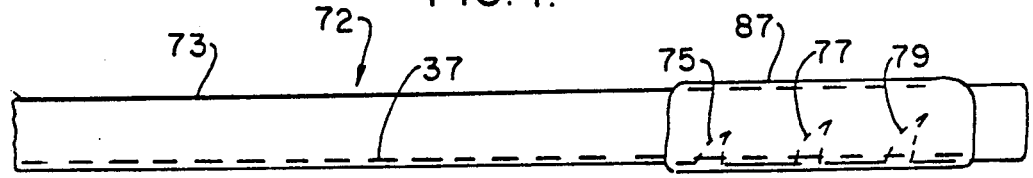
FIG. 8 is a view similar to FIG. 4A showing a covering over the gaps.

For some applications, it may be preferred that the gaps be covered. FIG. 8 shows a layer of material 87 covering the gaps. It should be realized that the physical appearance of layer 87 in FIG. 8 is illustrative only. The appearance will differ depending upon how layer 87 is made. It can be formed by dipping, fusing, or heat shrinking, for example.

Similarly, the gaps themselves may be formed in a number of different ways. They can be laser cut, water jet cut, punched, or formed by any other suitable procedure.

Figure 9:
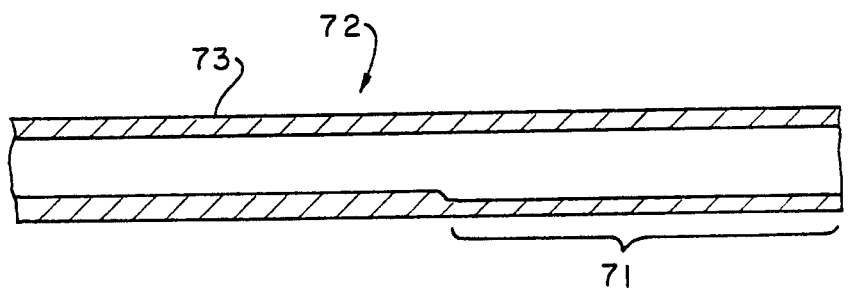
FIG. 9 is a sectional view illustrating an alternative way to cause the catheter to bend in a desired direction.

In addition, various ways can be used to form the predetermined region of weakness 71, either alone or in combination with the gaps. For example, FIG. 9 shows a region of weakness 71 formed by reducing the thickness of the sheath/catheter wall at the predetermined region of weakness. Or, the predetermined region of weakness may be formed by having a portion of the wall which is chemically different from the tube wall elsewhere, or otherwise differs in some way from the rest of the sheath/catheter wall. This is accomplished, for example, by leaching material out of the appropriate portion of the sheath/catheter wall to form the region of weakness, or by using a different material in that region which is weaker than the material which makes up the rest of the sheath/catheter wall.

It should be appreciated that when gaps 75, 77 and 79 are cut into a straight sheath/catheter, and the layer 87 put over those gaps, there is the possibility that layer 87 material will bulge into the inner lumen of the sheath-/catheter when the distal end is curved by application of tension to wire 37.

Figure 10:
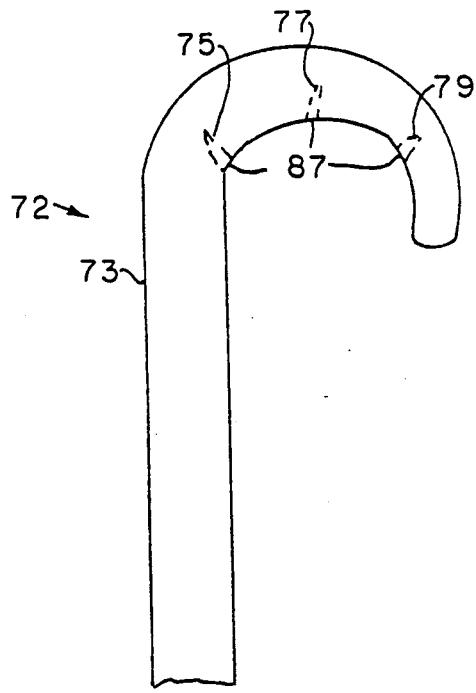
FIGS. 10 and 11 illustrate the method of construction of an alternative to that of FIGS. 4A-4D.

This bulging can be prevented if the distal end of the catheter tube is preformed into a curved shape with the gaps on the inner side of the preformed curve, as shown in FIG. 10. The gaps are then in their "rest position" when the distal end of the sheath/catheter is fully curved. A stretchable covering material 87 is then deposited over the gaps in this curved, "rest" position, so that the stretchable covering layer is substantially relaxed when the tube is disposed in a predetermined bent position.

Figure 11:
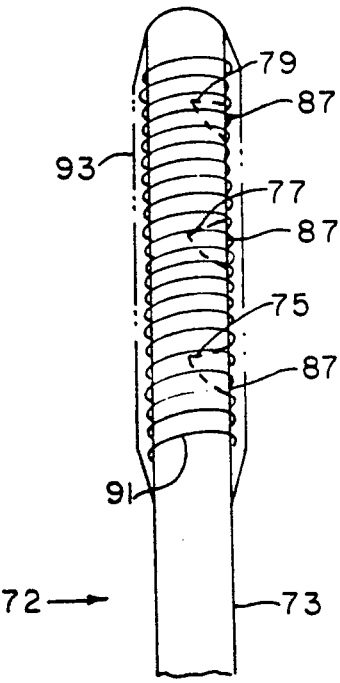

With this construction, the stretchable covering layer 87 is substantially in tension when the distal end of the sheath/catheter is straight, and the covering layer tends to pull the distal end back to the preformed, curved shape. To overcome this tendency, a spring (or other suitable device) 91 is provided for biassing the stretchable covering layer into a stretched position, as shown in FIG. 11. A jacket of material 93 is provided to cover the biassing spring.

Figures 12, 12A:
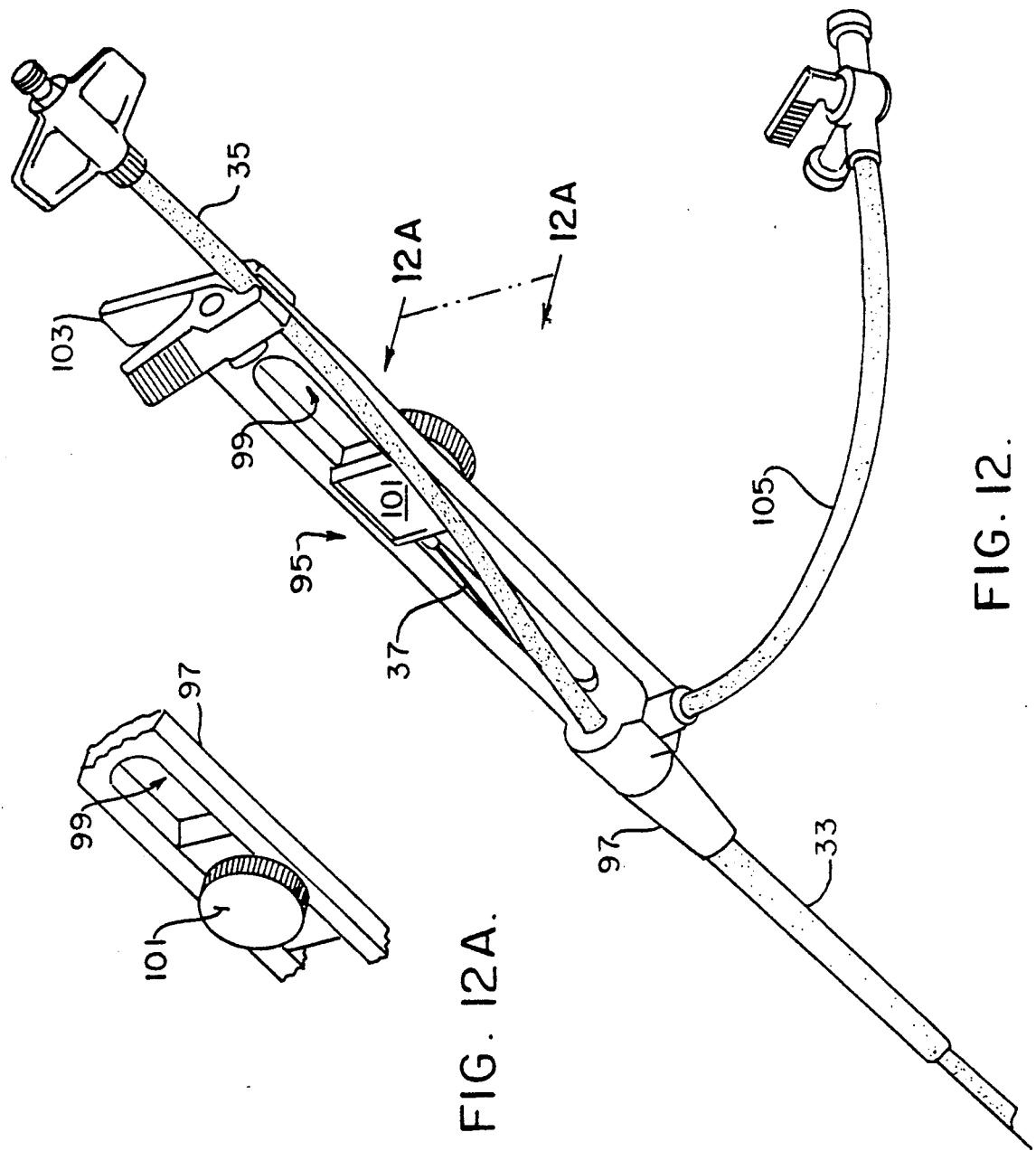
FIGS. 12 and 12A are perspective views illustrating an improved handle of the present invention.

Turning to FIGS. 12 and 12A, it is desirable to make the transformable catheter of the present invention as easy to use as possible. To facilitate this, a handle assembly 95 is provided which is an alternative to the structure shown in FIGS. 1C-1E. Handle assembly 95 includes a handle 97 fixedly secured to sheath 33. Handle 97 has a slot 99 formed therein in which rides a thumbwheel operated clamp 101 (shown in more detail in FIG. 12A). The body of the thumbwheel operated clamp is connected to wire 37, so that the user may manually adjust the tension on wire 37 by moving clamp 101 to the desired position in slot 99 and fix the clamp in that position to maintain the desired tension on the wire. Since the position of clamp 101 in slot 99 is infinitely variable, the tension on wire 37 is also continuously variable over the desired range.

The construction of FIG. 12 also provides for infinite variation in the rotational and longitudinal positioning of catheter 35 with respect to handle 97. The handle has secured thereto a spring clamp 103. Catheter 35 may be held by the jaws of spring clamp 103 (or other suitable device) in any desired rotational or longitudinal position, as controlled by the user. The jaws of the clamp are merely opened to allow the user to move the catheter longitudinally and/or rotationally, and then closed on the catheter to hold it in the new desired position.

Also shown in FIG. 12 is an auxiliary line 105 which constitutes means (in combination with a syringe, for example) for forcing fluid between the sheath 33 and the catheter 35. Such flushing helps to prevent the formation of clots, for example.

In view of the above, it will be seen that the various objects and features of the present invention are achieved and other advantageous results obtained. The examples of the present invention disclosed herein are intended to be illustrative, and are not to be construed in a limiting sense.

What is claimed is:

1. A combination catheter comprising:
   a catheter tube having a wall and an internal lumen extending substantially through the length of the catheter tube, said catheter tube having an outside diameter sufficiently small so that the catheter tube may be inserted into the human body, said catheter tube having a proximal end and a distal end;
   at least one wire running from the proximal end of the catheter tube to the vicinity of the distal end of the catheter tube, said wire being connected to the catheter tube adjacent the distal end so as to allow the distal tip of the catheter tube to be deflected upon movement of said wire;
   said catheter tube having a substantially uniform transverse cross section throughout a substantial part of its length, the catheter tube wall adjacent the distal end of the catheter tube having therein on one side of the longitudinal axis of the catheter tube a predetermined region of weakness, whereby upon tension being applied to the wire the distal end of the catheter tube bends in the direction of the predetermined region of weakness;
   an inner surgical element disposed in the lumen of the catheter tube, said inner surgical element being rotationally and axially movable in the lumen of the catheter tube, said inner surgical element being sufficiently pliable to bend upon bending of the catheter tube; and
   manually operable means for fixing the inner element in desired rotational positions with respect to the catheter tube;
   said predetermined region of weakness being formed by gaps in the wall of the catheter tube, at least some of the gaps having a generally crescent moon shape.

2. A combination catheter comprising:
   a catheter tube having a wall and an internal lumen extending substantially through the length of the catheter tube, said catheter tube having an outside diameter sufficiently small so that the catheter tube may be inserted into the human body, said catheter tube having a proximal end and a distal end;
   at least one wire running from the proximal end of the catheter tube to the vicinity of the distal end of the catheter tube, said wire being connected to the catheter tube adjacent the distal end so as to allow the distal tip of the catheter tube to be deflected upon movement of said wire;
   said catheter tube having a substantially uniform transverse cross section throughout a substantial part of its length, the catheter tube wall adjacent the distal end of the catheter tube having therein on one side of the longitudinal axis of the catheter tube a predetermined region of weakness, whereby upon tension being applied to the wire the distal end of the catheter tube bends in the direction of the predetermined region of weakness;
   an inner surgical element disposed in the lumen of the catheter tube, said inner surgical element being rotationally and axially movable in the lumen of the catheter tube, said inner surgical elements being sufficiently pliable to bend upon bending of the catheter tube; and
   manually operable means for fixing the inner element in desired rotational positions with respect to the catheter tube;
   said predetermined region of weakness being formed by gaps in the wall of the catheter tube, at least some of the gaps having a generally diamond shape.

3. A combination catheter comprising:
   a catheter tube having a wall and an internal lumen extending substantially through the length of the catheter tube, said catheter tube having an outside diameter sufficiently small so that the catheter tube may be inserted into the human body, said catheter tube having a proximal end and a distal end;

at least one wire running from the proximal end of the catheter tube to the vicinity of the distal end of the catheter tube, said wire being connected to the catheter tube adjacent the distal end so as to allow the distal tip of the catheter tube to be deflected upon movement of said wire;

said catheter tube having a substantially uniform transverse cross section throughout a substantial part of its length, the catheter tube wall adjacent the distal end of the catheter tube having therein on one side of the longitudinal axis of the catheter tube a predetermined region of weakness, whereby upon tension being applied to the wire the distal end of the catheter tube bends in the direction of the predetermined region of weakness;

an inner surgical element disposed in the lumen of the catheter tube, said inner surgical element being rotationally and axially movable in the lumen of the catheter tube, said inner surgical element being sufficiently pliable to bend upon bending of the catheter tube; and manually operable means for fixing the inner element in desired rotational positions with respect to the catheter tube;

said predetermined region of weakness being formed by gaps in the wall of the catheter tube, at least some of the gaps having a generally arrowhead shape.

4. A transformable catheter comprising:

a sheath having a diameter sufficiently small so that the sheath may be inserted into blood vessels of the human body, said sheath having a length which is a substantial fraction of the entire length of the transformable catheter, and having a bore therethrough running substantially from the proximal end of the sheath to the distal end of the sheath;

a preformed inner catheter having a complex curve formed into the distal end thereof, said preformed catheter being sized to fit in the sheath bore and being axially and rotationally movable with respect to the sheath in the bore, said sheath being sufficiently rigid and the inner catheter being sufficiently pliable so that withdrawal of the inner catheter into the sheath substantially straightens out the portion of the complex curve of the distal tip disposed within the sheath, said distal tip resuming its complex curved shape upon movement thereof out of the sheath bore, said inner catheter having a length substantially corresponding to the length of the transformable catheter;

at least one wire running from the proximal end of the sheath to the vicinity of the distal end of the sheath, said wire being connected to the sheath adjacent the distal end so as to allow the distal tip of the sheath to be deflected upon movement of said wire;

whereby by suitable manipulation of the wire and of the inner catheter with respect to the sheath the shape of the exposed portion of the distal end of the inner catheter may be reformed and transformed to any of a variety of shapes as described by the user;

said sheath having at its distal end a predetermined region of weakness so that upon tension being applied to the wire, the distal end of the sheath bends in the direction of the predetermined region of weakness;

the distal end of the sheath being preformed into a curved shape with a plurality of gaps on the inner side of the preformed curve;

the gaps being covered by a stretchable covering layer, said stretchable covering layer being substantially relaxed when the sheath is disposed is a predetermined bent position;

further including means for biassing the stretchable covering layer into a stretched position, wherein the means for biassing includes a spring disposed about the distal end of the sheath.

5. The transformable catheter as set forth in claim 4 further including a jacket of material covering said spring.

6. A method of directing and shaping an inner curved element by interaction with a curvable outer catheter tube in which the inner curved element is disposed, said outer catheter tube having a diameter sufficiently small so that the catheter tube may be inserted into the human body, having a length substantially the length of the inner element, and having a bore therethrough running substantially from the proximal end of the catheter tube to the distal end of the catheter tube, said inner curved element being disposed in said bore and being axially movable with respect to the catheter tube in the bore, said catheter tube being sufficiently rigid and the inner element being sufficiently pliable so that withdrawal of the inner element into the catheter tube substantially irons out the portion of the curve of the distal tip of the inner element disposed within the catheter tube, said distal tip resuming its curved shape upon movement thereof out of the catheter tube bore, said inner element being somewhat longer than the length of the catheter tube, said catheter tube having at its distal end a longitudinally extending predetermined region of weakness, the distal end of the catheter tube being curvable in the direction of the predetermined region of weakness, said method comprising the steps of:

disposing the inner element at a first rotational position with respect to the predetermined region of weakness of the catheter tube such that the distal end of the inner element is disposed substantially in a plane containing the longitudinal axis of the predetermined region of weakness, and extending the inner element distally outwardly with respect to the catheter tube to generate the desired element shape;

disposing the inner element at a second rotational position with respect to the predetermined region of weakness of the catheter tube, said second rotational position being substantially 180 degrees from the first rotational position, and extending the inner element distally outwardly with respect to the catheter tube to generate the desired element shape; and disposing the inner element at a third rotational position with respect to the predetermined region of weakness of the catheter tube, said third rotational position being disposed intermediate the first and second rotational positions, and extending the inner element distally outwardly with respect to the catheter tube to generate the desired element shape.

7. The method as set forth in claim 6 wherein said catheter tube also has at least one wire running from the proximal end of the catheter tube to the vicinity of the distal end of the catheter tube, said wire being connected to the catheter tube adjacent the distal end such that the distal tip of the catheter tube is deflected upon tension being applied to said wire to modify the shape of the inner element carried by the catheter tube, further including the step of applying tension to said wire to deflect the distal end of the catheter tube an amount sufficient to form the inner element into a desired shape.

8. A method of directing and shaping an inner element by interaction with an outer catheter tube in which the inner element is disposed, said outer catheter tube in which the inner sufficiently small so that the catheter tube may be inserted into the human body, having a length substantially the length of the inner element, and having a bore therethrough running substantially from the proximal end of the catheter tube to the distal end of the catheter tube, said inner element being disposed in said bore and being axially movable with respect to the catheter tube in the bore, said catheter tube being sufficiently rigid and the inner element being sufficiently pliable to that withdrawal of the inner element into the catheter tube causes the portion of the distal tip of the inner element disposed within the catheter tube to assume the shape of the catheter tube at that location, said distal tip resuming its shape upon movement thereof out of the catheter tube bore, said inner element being somewhat longer than the length of the catheter tube, said catheter tube having at its distal end a longitudinally extending predetermined region of weakness so that the distal end of the catheter tube is curvable in the direction of the predetermined region of weakness, said method of comprising the steps of:
 moving the combination of the catheter tube and the inner element through passage in the human body with the distal end of the inner element disposed distally of the distal end of the catheter tube so that the distalmost portion of the combination is formed by the distal end of the inner element; and
 deflecting the distal end of catheter tube such that the distal end of the inner element takes a desired shape.

9. The method as set forth in claim 8 wherein said catheter tube has at least one wire running from the proximal end of the catheter tube to the vicinity of the distal end of the catheter tube, said wire being connected to the catheter tube adjacent the distal end such that the distal tip of the catheter tube is deflected upon tension being applied to said wire to modify the shape of the inner element carried by the catheter tube, further including the step of applying tension to said wire to deflect the distal end of the catheter tube an amount sufficient to form the inner element into a desired shape.

10. A method of directing an inner element by interaction with an outer catheter tube in which the inner element is disposed, said outer catheter tube having a diameter sufficiently small so that the catheter tube may be inserted into the human body, having a length substantially the length of the inner element, and having a bore therethrough running substantially from the proximal end of the catheter tube to the distal end of the catheter tube, said inner element being disposed in said bore and being axially movable with respect to the catheter tube in the bore, said catheter tube being sufficiently rigid and the inner element being sufficiently pliable so that withdrawal of the inner element into the catheter tube causes the portion of the distal tip of the inner element disposed within the catheter tube to assume the shape of the catheter tube at that location, said distal tip resuming its shape upon movement thereof out of the catheter tube bore, said inner element being somewhat longer than the length of the catheter tube, said catheter tube being fixable with respect to the inner element, said method of comprising the steps of:
 moving the combination of the catheter tube and the inner element through a passage in the human body with the distal end of the inner element disposed distally of the distal end of the catheter tube so that the distalmost portion of the combination is formed by the distal end of the inner element;
 fixing the inner element with respect to the catheter tube at the proximal end thereof; and
 rotating the catheter tube to provide torque to the inner element throughout its length.

* * * * *

UNITED STATES PATENT AND TRADEMARK OFFICE
CERTIFICATE OF CORRECTION

PATENT NO. : 5,304,131
DATED : April 19, 1994
INVENTOR(S) : Larry D. Paskar

It is certified that error appears in the above-indentified patent and that said Letters Patent is hereby corrected as shown below:

Column 13, line 10, delete "in which the inner" and insert --having a diameter--.

Column 13, line 32, add "a" after through.

Signed and Sealed this

Twentieth Day of September, 1994

Attest:

BRUCE LEHMAN

*Attesting Officer*   *Commissioner of Patents and Trademarks*